(12) United States Patent
Lauridsen et al.

(10) Patent No.: US 8,348,668 B2
(45) Date of Patent: Jan. 8, 2013

(54) DENTAL IMPLANT, AND SUPERSTRUCTURE THEREFORE

(75) Inventors: Christian Lauridsen, Limhamn (SE); Bo Ekström, Bunkeflostrand (SE); Mats Ljungberg, Malmö (SE)

(73) Assignee: Simply Dental AB, Limhamn (SE)

( * ) Notice: Subject to any disclaimer, the term of this patent is extended or adjusted under 35 U.S.C. 154(b) by 0 days.

(21) Appl. No.: 13/120,555

(22) PCT Filed: Sep. 24, 2009

(86) PCT No.: PCT/SE2009/051067
§ 371 (c)(1),
(2), (4) Date: Apr. 15, 2011

(87) PCT Pub. No.: WO2010/036197
PCT Pub. Date: Apr. 1, 2010

(65) Prior Publication Data
US 2011/0189635 A1 Aug. 4, 2011

Related U.S. Application Data

(60) Provisional application No. 61/100,153, filed on Sep. 25, 2008.

(30) Foreign Application Priority Data

Sep. 25, 2008 (SE) ........................... 0802034
Jun. 18, 2009 (SE) ........................... 0950478

(51) Int. Cl.
*A61C 8/00* (2006.01)
(52) U.S. Cl. ...................................... 433/173
(58) Field of Classification Search .................. 433/173, 433/174, 175
See application file for complete search history.

(56) References Cited

U.S. PATENT DOCUMENTS

| 3,732,621 | A | | 5/1973 | Bostrom |
| 4,793,808 | A | | 12/1988 | Kirsch |
| 5,527,182 | A | * | 6/1996 | Willoughby ............. 433/172 |
| 5,564,922 | A | * | 10/1996 | Rosa et al. ............... 433/173 |
| 5,667,384 | A | | 9/1997 | Sutter et al. |
| 5,997,299 | A | | 12/1999 | Unger |

FOREIGN PATENT DOCUMENTS

| DE | 19653229 A1 | 6/1998 |
| DE | 20102531 U1 | 6/2002 |
| DE | 10101907 A1 | 7/2002 |
| EP | 0923910 A1 | 6/1999 |
| WO | 9309728 | 5/1993 |
| WO | 9406369 | 3/1994 |

\* cited by examiner

*Primary Examiner* — Ralph Lewis
(74) *Attorney, Agent, or Firm* — Capitol City TechLaw

(57) ABSTRACT

This invention pertains to a superstructure (300) for a dental implant. The superstructure comprises a fastening portion (30) with a joint socket in form of a spherically shaped cavity with a fastening surface (32), and a main portion (31). This superstructure (300) is intended to be joined to an osseointegrated dental implant via the fastening portion (30). The main portion (31) comprises a lead-through (110) for receiving a sleeve (111) or a screw hole (55), wherein part of said lead-through (110) or part of said screw hole (55) forms an opening in the fastening surface (32), such that there is a perpendicularly distance between the center of the spherical cavity and the central axis of the lead-through (110) or of the screw hole (55).

13 Claims, 9 Drawing Sheets

DENTAL IMPLANT, AND SUPERSTRUCTURE THEREFORE

FIELD OF THE INVENTION

This invention pertains in general to the field of dental implants. More particularly the invention relates to a dental implant for supporting a dental prosthesis or dental superstructure, said dental implant comprising, along its longitudinal axis, a securing portion to be anchored in the jawbone, and a ball or joint socket; a dental implant adapter, with a fastening portion for fastening the dental implant adapter to a ball or joint socket of a dental implant, and a dental implant adapter head; and a superstructure, with a main body, and receiving means for receiving a ball or joint socket of a dental implant or a dental implant adapter.

BACKGROUND OF THE INVENTION

Implant systems of today attempts to restore the patient to normal function, comfort, aesthetic, speech and health regardless of the current oral condition. These implant systems are based on the implantation of dental implants, such as dental implants made of biocompatible titanium, through insertion into the patient's jawbone. In this respect, the use of biocompatible titanium started in Sweden as early as 1950, and has since then been further developed and spread worldwide. During the 1980's a number of implant systems entered the world market. Methods are known in the art to attach a dental superstructure to an implant. These may use dental cement. A couple of methods are based on the use of a screw member. These screw members can attach the superstructure to the implant, either directly or via spacers.

When a patient has been without tooth/teeth for a period of time, the jawbone starts to degenerate, since the jawbone is not under strain from masticatory forces. This results in less bone material for the proper anchoring of a dental implant. To find enough bone for optimal implantation, the dental implant sometimes has to be angled so that the longitudinal axis of the dental implant projects out of the mouth.

Fixing a superstructure with dental cement is complicated due to factors, such as varied drying time of the cement, difficulties in fixating the superstructure while the dental cement is drying, and problems to adjust a dental superstructure once the dental cement has dried. If a screw member is used, it necessitates that the mouth of the screw channel is placed on a visual surface of the dental superstructure. Also, the optimum placement of the implant, due to the present dental situation, often results in a non-optimum placement of the dental superstructure in terms of the patient's aesthetics, phonetics and bite. Furthermore, it is complicated to manufacture superstructures adapted for dental implants with diverting securing angles, since spacers and/or integrated spacers have to be exactly configured in respect of the different angles of the dental implants. This may also result in a complicated mounting procedure of the superstructure, if two closely located dental implants deviant directions.

The means already known in the art for achieving this goal include the use of angled spacers and dental superstructures attached to the implant with adhesive or with other techniques not based on the use of a screw member. The angled spacers have many drawbacks and are characterized by adding significant height to the superstructure. It also results in an increased complexity of the attachment of the superstructure to the implant.

Also, when an implant has already been implanted, and a satisfactory osseointegration of the implant has been obtained, it would be of great damage to exchange such an implant with another implant, better suited for attachment of structures or spacer elements needed in changed circumstances for the patient. This may be the case if the patient is in need of some kind of reconstruction of the dental structure, such as for example in case of loosing yet another tooth. In this case it would be better to have a dental implant better suited for adaptation in respect of other implants, spacer elements, and/or superstructures in the mouth of the patient.

Hence, an improved dental implant, dental implant adapter, and superstructure would be advantageous, and in particular a dental implant, dental implant adapter, and superstructure allowing for a good fit of the superstructure to the gum, a simpler, faster and cheaper production method of said superstructure, cost-effectiveness, more simple assembly, greater freedom of placement of a dental implant, for enabling use of an implant placed optimally with regard to the dental situation, that is, the anatomy of the jawbone, while still allowing the dental superstructure to be applied in an optimal way to said implant, such that the mouth of a screw channel not is visible from outside the mouth of the patient, would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a superstructure for a dental implant, comprising a fastening portion, comprising a joint socket in form of a spherically shaped cavity with a fastening surface, and a main portion, which superstructure is intended to be joined to an osseointegrated dental implant via the fastening portion, characterized in that the main portion comprises a lead-through adapted for receiving a sleeve or a screw hole, wherein part of said lead-through or part of said screw hole form an opening in the fastening surface, and in that there is a perpendicularly distance between the center of the spherical cavity and the central axis of the lead-through or of the screw hole;

and a dental implant system, comprising a dental implant and a superstructure joined with a ball or joint socket.

The general solution according to the invention is to provide a solution wherein a dental superstructure may be fastened correctly independent of the angle, with which the dental implant is secured in the jaw bone.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which FIG. 1 is an illustration of a dental implant according to some embodiments.

FIG. 2 is an illustration of a dental implant adapter according to some embodiments.

FIG. 3 is an illustration of a dental superstructure according to some embodiments.

FIG. 8A is showing the implant from the side and FIG. 8B is showing the implant from the top.

FIG. 9A is showing the implant from the side and FIG. 9B is showing the implant from the top.

FIG. 10A is showing the implant from the side and FIG. 10B is showing the implant from the top.

DESCRIPTION OF EMBODIMENTS

Figure 1A:
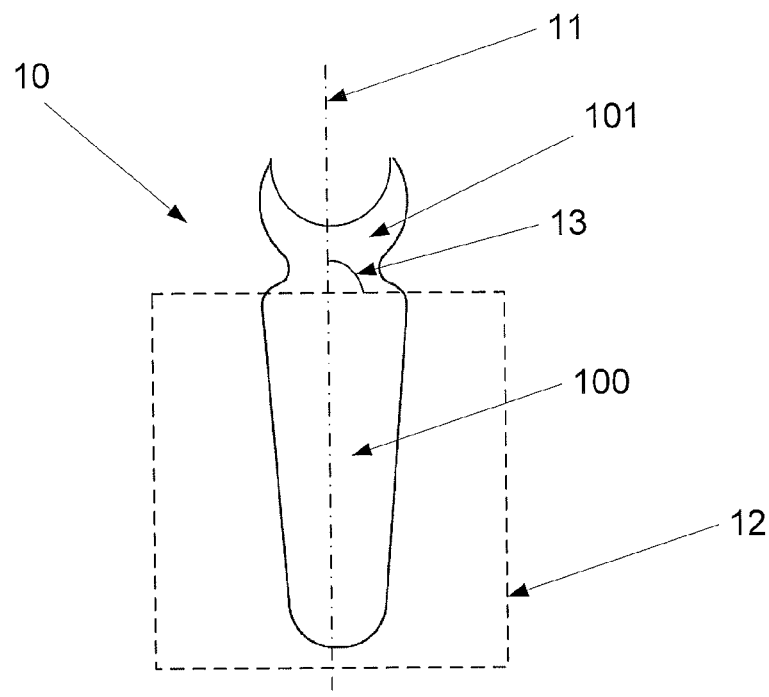
FIG. 1A is showing an embodiment with joint socket and FIG. 1B is showing an embodiment with ball socket.

The following description focuses on embodiments applicable to a dental implant, and in particular to a dental implant for supporting a dental prosthesis or dental superstructure, comprising along its longitudinal axis, a securing portion to be anchored in the jawbone with an angle in relation to the jawbone, and a fastening portion with an accessible surface and superstructures adapted therefore. Also, embodiments of a dental implant adapter with a fitting portion for securing the dental implant adapter to a fastening portion of a dental implant will be described.

According to one embodiment, illustrated in FIG. 1, a dental implant 10 is disclosed. The dental implant has a first and a second end along a longitudinal axis 11. The dental implant may be in one piece, such as solid or massive, such that there are no interfaces in between the different parts of the dental implant. The dental implant comprises a securing portion 100 to be anchored in the jawbone 12 of a patient with an angle 13 in relation to the vertical plane of the jawbone. The securing portion 100 may be a threaded portion along its longitudinal axis towards the first end. The anchoring in the jawbone is possible due to osseointegration, well known in the art. The dental implant further comprises a fastening portion 101, for fastening a superstructure to said dental implant, towards the second end of the dental implant. The fastening portion 101 has a positively or negatively spherical shape. Thus, the fastening portion 101 may be a ball or joint socket, as will be discussed in further detail below. When the securing portion 100 has been anchored in the jawbone 12 of the patient, the fastening portion is suitable for connection to a superstructure independent of the angle 13 at which the dental implant 10 is anchored in the jawbone 12. The dental implant 10 may comprise or constitute a driving portion in the second end of the dental implant, which driving portion is adapted to engage a driving tool. The driving portion may be selected from the group comprising a female groove or recess for cooperating with a chisel or screwdriver head; hex recess; polygonal recess; a recess with an internal threading etc.

When the driving portion is a recess with an internal threading the dental implant may be attached to the driving tool prior to the insertion of the dental implant in the jawbone, whereby the driving tool may fasten the dental implant without having to loosen and re-grip the driving portion. This may also give the advantage that the dental implant is firmly secured on the driving tool which makes it more simple to attach to the jawbone. It may also be safer for the patient, since there are no loose parts, which may be swallowed. The driving tool may be manually or automatically driven, such as by a screwdriver or dental drill, to rotate the dental implant in a selected rotational direction to secure or remove a threaded securing portion 100 from the jawbone tissue. The fastening portion 101 is arranged adjacent or in close proximity to the securing portion 100, such that the distance between the fastening portion 101 and the bone tissue may be kept small, when the dental implant is anchored in the jawbone 12. If the fastening portion 101 and the securing portion 100 are of approximately the same diameter, a waist may be provided there between, especially if the fastening portion 101 is a ball socket.

In an embodiment according to FIG. 1A, the fastening portion 101 of the dental implant 10 is a joint socket. The joint socket provides a negative spherical shape. The negative spherical shape provides a concave surface area in the second central end of the dental implant. This concave surface area is configured to engagingly interact with a positive spherical shape on a superstructure, such as a ball shape. The radius of the concave surface area may be selected such that it may receive the positive spherical shape on the superstructure, such that the angle between a central axis of the dental implant does not have to be aligned with a central axis of a protrusion on the superstructure bearing the positive spherical shape.

According to one embodiment, the angle between the longitudinal axis 11 of the dental implant and the radius drawn from the top end of the concave surface, in relation to the centre of the spherical geometry for the concave surface of the joint socket, is more than 90°, seen from the first end of the dental implant 10. Thus, in a cross section of the dental implant, along a longitudinal plane, the top ends of the concave surface have a distance above a horizontal plane, running through the centre of the sphere and perpendicular to the longitudinal plane, which is shorter than the diameter of the sphere. To this end, the engagement between the dental implant, and a superstructure attached there to, may be ensured.

The joint socket provides the advantage of not having to protrude from the jaw bone. This may give a very tight fit between the dental implant and a dental superstructure secured thereon. An advantage of a joint socket on the dental implant is that the dental superstructure may be connected with a ball socket, which does not require very much space. An advantage of the joint socket on the dental implant is that it is possible to work with smaller widths on the dental superstructures, which is an advantage when having single-teeth superstructures. Thus, the joint socket provides anatomical connection. This may be important in cases with high aesthetic demands. Furthermore, the joint socket may be designed so that the driving portion may be hidden within the negative spherical shape. This may give a more hygienic solution, since it protects the driving portion from organic particles, which may otherwise be trapped in the driving portion and rot. Alternatively, the joint socket may be designed so that the driving portion is not a part of the negative spherical shape. This flexibility may give rise to a range of possible driving portion designs, which will be appreciated by a person skilled in the art. Also, the solution where the joint socket provides a negative spherical shape is useful when a combination between natural teeth and implants are desirable. This is because the solution is particularly suited to handle smaller superstructures replacing one tooth or two teeth.

Figure 1B:
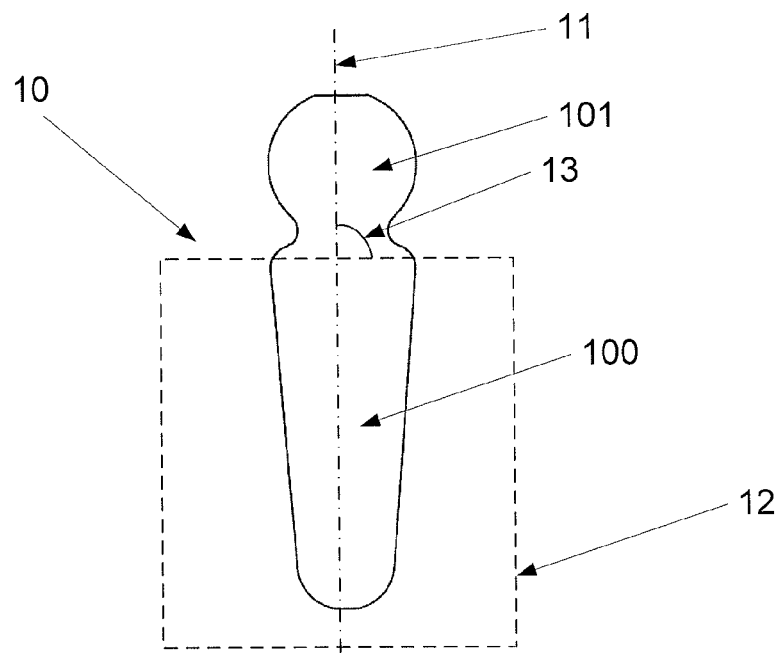

In a further embodiment according to FIG. 1B, the fastening portion 101 is a ball socket. The ball socket provides a positive spherical shape. The positive spherical shape provides a convex surface area in the second central end of the dental implant. This convex surface area is configured to engagingly interact with a negative spherical shape on a superstructure. The radius of the convex surface area may be selected such that it mat receive the negative spherical shape on the superstructure, such that the angle between a central axis of the dental implant does not have to be aligned with a central axis, such as for example an axis coinciding with the central axis of a screw hole, in the superstructure bearing the negative spherical shape. Such screw hole may for example have a central axis with a direction parallel to, and perhaps coinciding with, the corda of the negative spherical shape of the superstructure. This will be further described below. The ball socket provides the advantage of easy cleaning, since it may be provided without any depressions. Furthermore, since the ball socket is protruding from the jaw bone, it provides easy access by, e.g. a mould, when making an impression for the positioning of the implant. The ball socket design also allow angle-independent fitting of a superstructure to multiple ball sockets. This solution is very suitable for cases where the superstructure is designed to replace all teeth.

The fastening portion 101 in form of a ball or joint socket may be provided with splines, grooves, or in other ways a rugged surface, to increase the friction between the ball or joint socket and another surface adjacently configured thereto. Such adjacently configured The angle 13, with which the dental implant 10 is anchored in the jawbone, may be between 0° and 90° in respect of a desired final horizontal axis of the superstructure. The desired final horizontal axis is the axis along which it is desired that the superstructure be aligned. This may depend on the physical properties of the patient and vary from case to case. The wide range of the angle 13 overcomes the problems related to degeneration of jawbones which may occur when the patient has been without tooth/teeth for a period of time, since it is possible to find an angle which allow the securing portion 100 to find enough bone material to be properly anchored in the jaw and still be suitable for providing support for a superstructure with a specific desired final horizontal axis. Furthermore, the angle-independent connectivity of the dental implant 10 alleviates the need for angular spacers. This in turn allows less complicated installation with fewer parts. Fewer parts may lead to safer mounting of the dental implant, since there are fewer possibilities for the patient to inhale or otherwise ingest the parts. Furthermore, fewer parts may allow easier assembly.

Figure 2A:
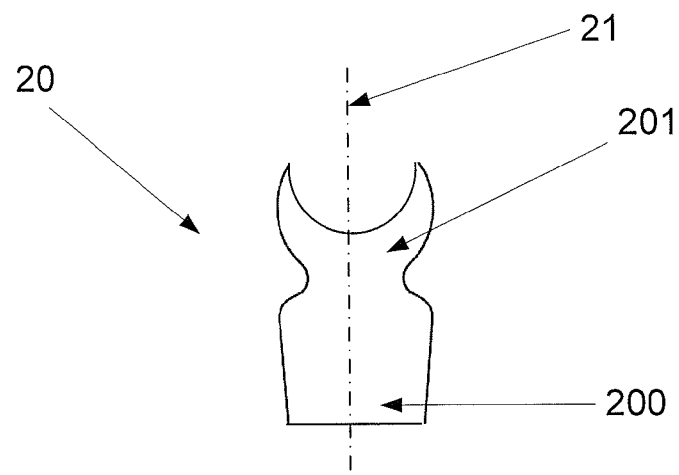
FIG. 2A is showing an embodiment with joint socket and FIG. 2B is showing an embodiment with ball socket.
Figure 2B:
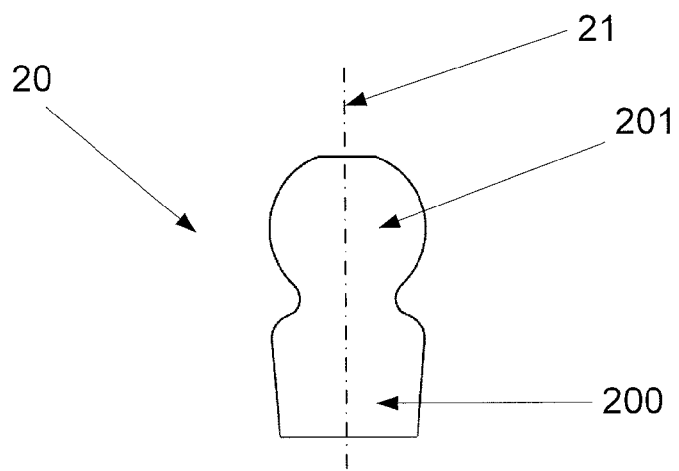

If, however, the patient already has a dental implant according to prior art, but is in need of another implant according to the present invention, the first implant may be modified by a dental implant adapter. In an embodiment according to FIG. 2, a dental implant adapter 20 is shown. Along its longitudinal axis 21, towards the first end, the adapter has a fitting portion 200. The fitting portion 200 is suitable to be fitted on an osseointegrated dental implant. Furthermore, the adapter has a fastening portion 201 towards the second end, for fastening a superstructure to said dental implant, towards the second end of the dental implant adapter. The fastening portion 201 has a positively or negatively spherical shape. Thus, the fastening portion 201 may be a ball or joint socket, as described above. The fitting portion 200 may be designed to fit any dental implant product or dental implant system according to prior art. FIG. 2A is showing an embodiment with joint socket and FIG. 2B is showing an embodiment with ball socket.

In an embodiment according to FIG. 3, a dental superstructure 300 for a dental implant is disclosed. The superstructure comprises a fastening portion 30 and a main portion 31. The fastening portion 30 has a fastening surface 32 intended for fastening to a dental implant 10. The fastening portion 30 comprises a fastening part 33. This fastening part 33 may be activated, i.e. manipulated in order to fasten the fastening portion 30 to the dental implant 10 or the dental implant adapter 20. This fastening is achieve since the fastening part regulates the pressure that the fastening surface 32 exerts on the dental implant 10 or the dental implant adapter 20. Furthermore, the fastening may be controlled through control means 34, which are operably connected to the fastening part 33. The control means are suitable to activate the fastening part 33.

Figure 3A:
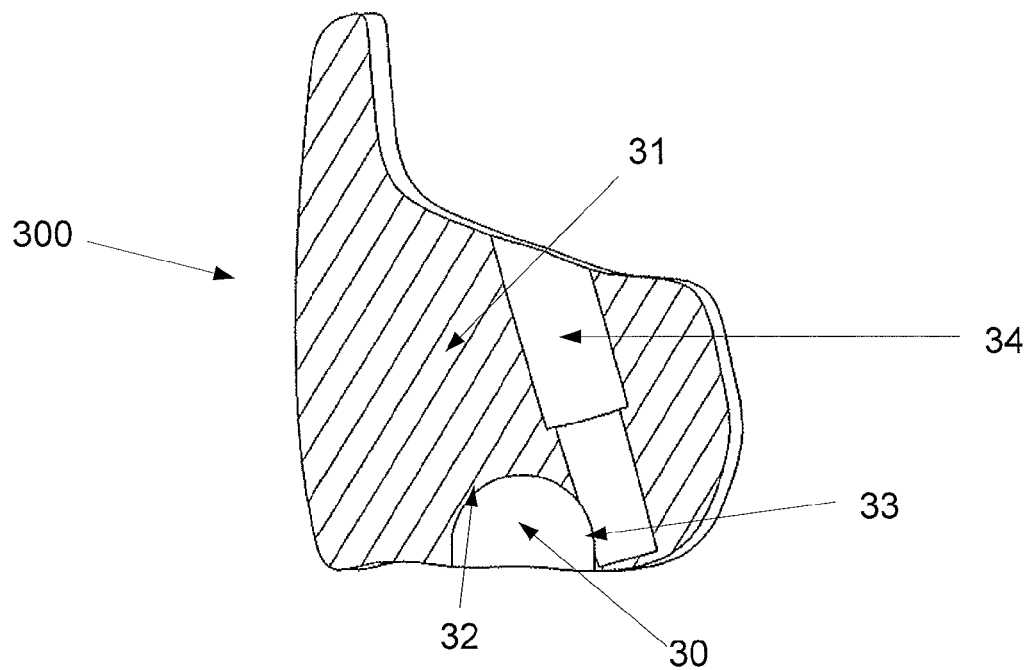
FIG. 3A is showing an embodiment with joint socket and FIG. 3B is showing an embodiment with ball socket.
Figure 3B:
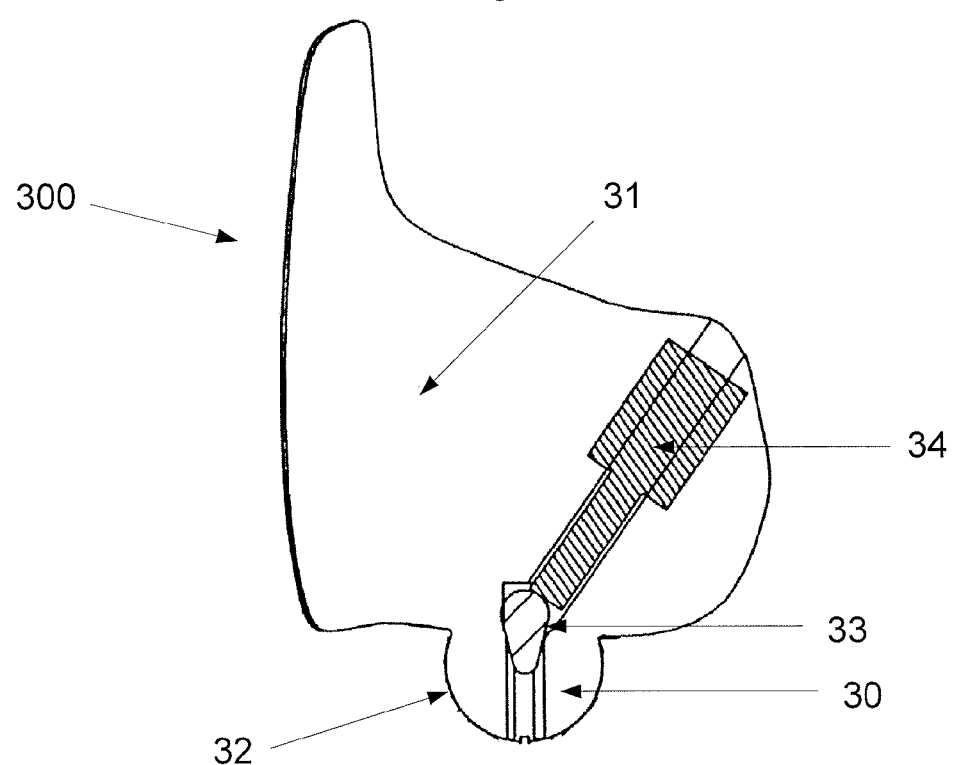

FIG. 3A is showing an embodiment with joint socket and FIG. 3B is showing an embodiment with ball socket.

According to one embodiment, the fastening surface 32 is fastened to the osseointegrated dental implant by one of the methods chosen from the group; clamp, friction grip, screw anchoring, screw anchoring and friction grip.

According to one embodiment, the abovementioned clamp is achieved by resilient materials, such as silicon. An advantage of this, is that the resilient materials provide a strong grip. Another advantage is that it facilitates easy application of the dental superstructure by e.g. lower the need for special equipment such as hydraulics, or lessening the number of movable parts used in the construction of the superstructure.

According to another embodiment, the abovementioned clamp is achieved by mechanical means. An advantage of this is ease of use, wherein only simple tools are needed for assembly.

Furthermore, according to one embodiment of the invention, a dental implant system is disclosed. The system may comprise a dental implant or a dental implant adapter and a dental superstructure. The dental implant/dental implant adapter and the dental superstructure may be designed according to any of the above embodiments so that they, when properly installed provide a secure fastening of the dental superstructure in the jawbone of the patient. The dental system has the advantage that it is working independently of the angle in relation to the jaw of the patient, which the dental implant is secured in the jaw. This also makes it easy to add new dental superstructures, or change the existing dental superstructure, if the patient for example looses more teeth, since the dental superstructures are easy to integrate.

Below, the interactions between dental implant/dental implant adapter and the dental superstructure will be further illustrated by use of non-limiting examples.

Figure 4:
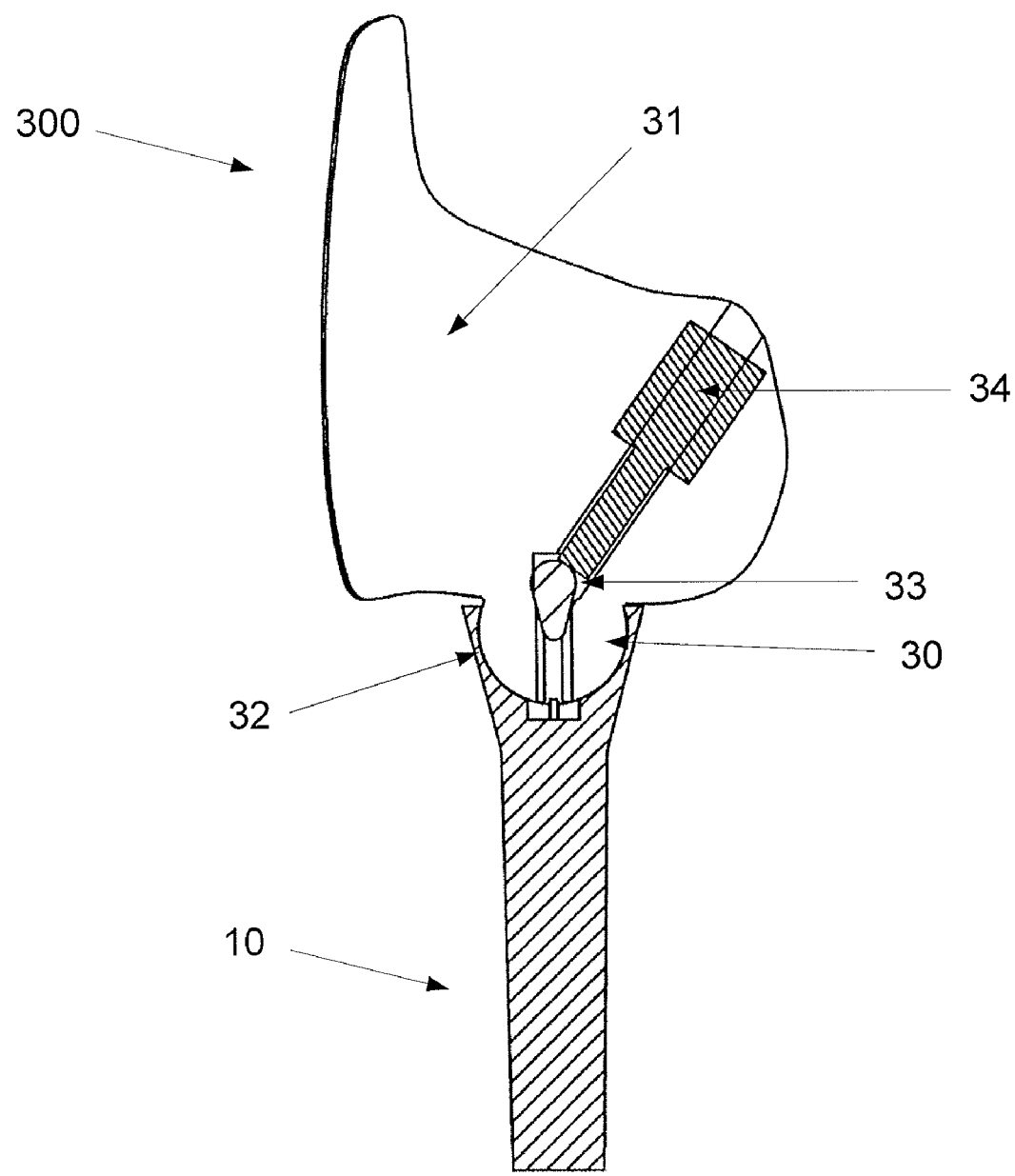
FIG. 4 is an illustration of the fastening according to one embodiment of the invention, where the implant has a joint socket.

In an embodiment according to FIG. 4, the fastening surface 32 of the fastening portion 30 of the dental superstructure 300 with ball socket consists of a vertical opening in the lower end of the fastening portion 30. In the end of the opening facing away from the fastening surface 32 is located an elastic ball. The elastic ball is affected by control means 34, e.g. a screw or a screw member, which changes the conformation of the elastic ball, which in turn expands the opening. This activated form of the dental superstructure makes the fastening surface 32 presses against the ball or joint socket of the dental implant 10 and thus fasten the superstructure in the dental implant 10.

Figure 5:
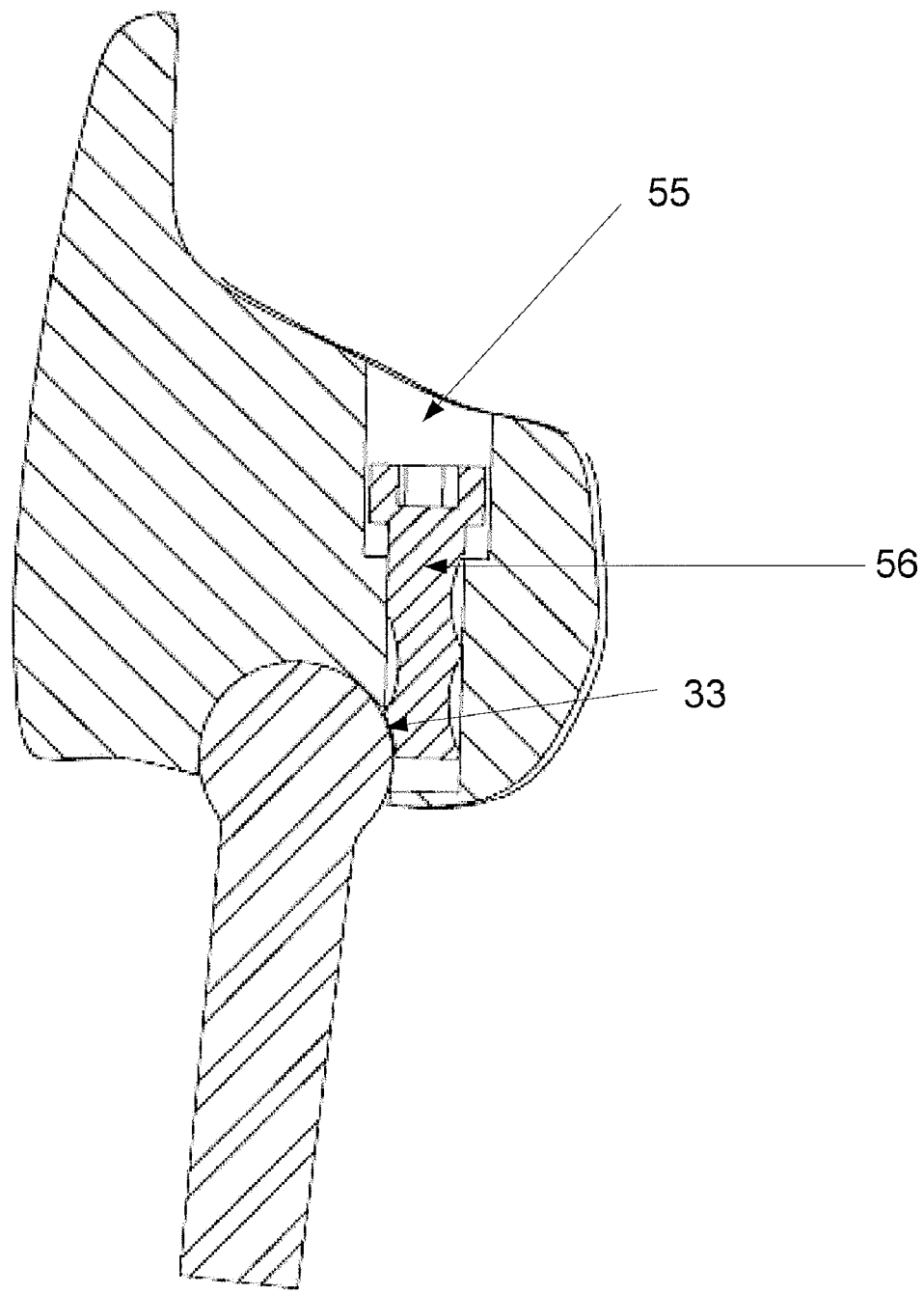
FIG. 5 is an illustration of the fastening according to one embodiment of the invention, where the implant has a ball socket.

In an embodiment according to FIG. 5, the interactions between dental implant/dental implant adapter and the dental superstructure with joint socket is illustrated. Here, the control means 34 comprise a screw hole 55 and a screw member 56. Part of the screw hole 55 forms an opening in the fastening surface 32, thus allowing the fastening part 33 to engage the dental implant 10. There is a perpendicularly distance between the center of the spherical cavity and the central axis of the screw hole 55, i.e. the screw hole 55 is not centered around the center of the spherical cavity of the joint socket.

Preferably, the central axis of the screw hole 55 does not cut any part of the spherically shaped cavity. The perpendicularly distance between the center of the spherical cavity and the central axis of the screw hole 55 is thus larger than the radius of the spherically shaped cavity. Accordingly, the ball socket of the dental implant 10 will only occupy the screw hole partly, when the superstructure is mounted on the dental implant. The screw member 56 is fitted in the screw hole such that it, when screwed in, activates the fastening part 33. When activated, the fastening part engages the dental implant 10, thus creating a pressure on the dental implant 10 to fasten the superstructure 300 to the dental implant 10 through frictional forces.

Figure 6:
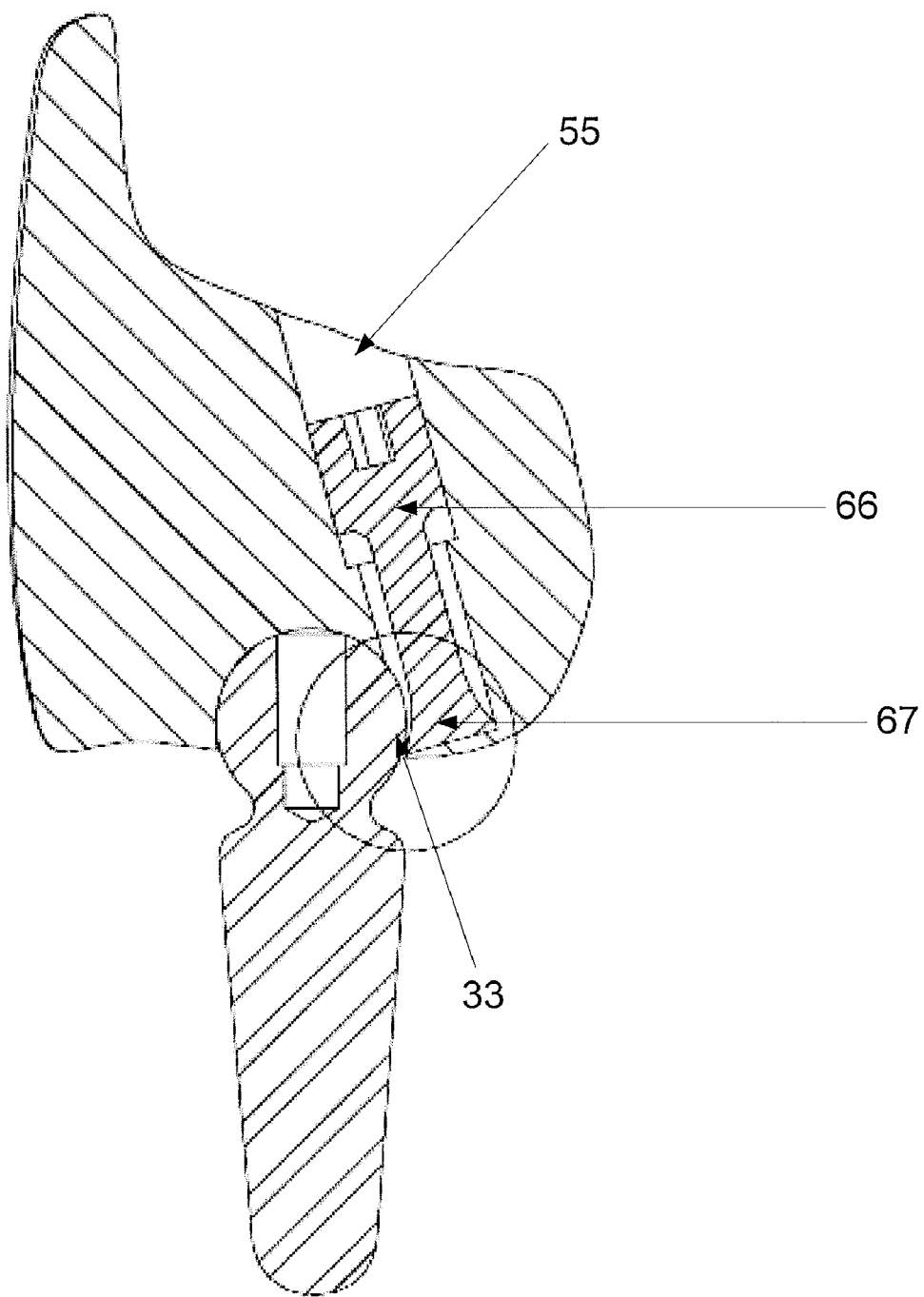
FIG. 6 is an illustration of the fastening according to another embodiment of the invention, where the implant has a ball socket.

Furthermore, in an embodiment according to FIG. 6, the control means 34 comprise a screw hole 55 and a second screw member 66. The second screw member 66 has a lower end 67, facing away from the driving portion. The lower end 67 has a larger diameter than the part of the screw with least diameter. Part of the screw hole 55 forms an opening in the fastening surface 32, thus allowing the fastening part 33 to engage the dental implant 10. The central axis of the screw hole 55 does not cut the fastening surface 32. There is a perpendicularly distance between the center of the spherical cavity and the central axis of the screw hole 55, i.e. the screw hole is not centered around the center of the spherical cavity of the joint socket.

Preferably, the central axis of the screw hole 55 does not cut any part of the spherically shaped cavity. The perpendicularly distance between the center of the spherical cavity and the central axis of the screw hole 55 is thus larger than the radius of the spherically shaped cavity. Accordingly, the ball socket of the dental implant will only occupy the screw hole partly 55, when the superstructure is mounted on the dental implant 10. The second screw member 66 is mounted such that it, when screwed out, activates the fastening part 33. When activated, the fastening part engages the dental implant 10, thus creating a pressure on the dental implant to fasten the superstructure to the dental implant through frictional forces.

The thread of the screw member 66 may be left hand threaded. The activation of the fastening part 33 is performed, as disclosed above, by screwing the second screw member 66 out, i.e. screwing the second screw member 66 such that the screw member head moves in an outwardly direction away from the fastening part 33. If the thread of the second screw member 66 is left hand threaded, screwing the second screw member 66 clock-wise will activate the fastening part 33. Use of a left hand threaded screw is advantageous as screwing clock-wise normally is associated with the tightening of screws. The thread in the screw hole 55, configured to engage with the thread of the second screw member 66, is thus adapted accordingly. This means that the thread in the screw hole 55 is configured to cooperate with a screw member with a left hand thread.

Similarly, it is preferred if the thread of the screw member disclosed in the embodiment of FIG. 5, i.e. the thread 56 is right hand threaded, to allow a tightening action by screwing the screw member clock-wise.

The size of the ball or joint socket may be selected, such that the contact surface between the ball or joint socket of the dental implant 10 and the superstructure 300 provides a satisfying friction force to keep the superstructure 300 from moving during use. In this respect the diameter of the ball or joint socket may be selected in the interval of 1.5 and 6.0 mm. The interval may be chosen based on the size of the tooth/teeth that is/are missing.

In one embodiment the diameter of the ball or joint socket may be selected in the interval of 2.5 to 4 mm.

Figure 11:
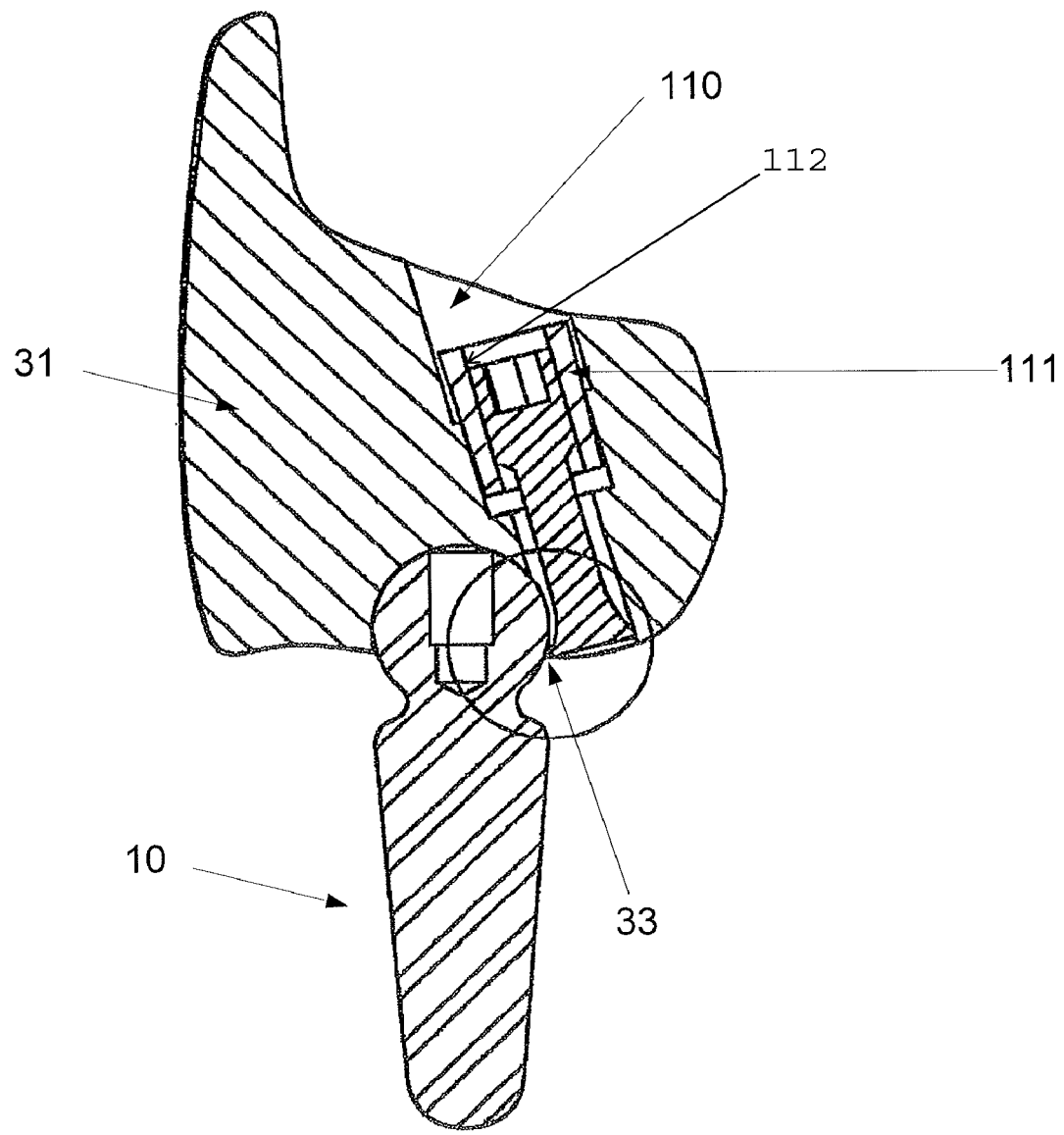
FIG. 11 is an illustration of the fastening according to one embodiment of the invention, where the implant has a ball socket and the superstructure comprises a sleeve.

In one embodiment, such as the one depicted in FIG. 11, the main portion 31 comprises a lead-through 110 adapted to receive and fasten a separate sleeve 111. Part of the lead-through 110 forms an opening in the fastening surface 32, thus allowing the fastening part 33 to engage the dental implant 10. The central axis of the lead-through 110 does not cut the fastening surface 32. There is a perpendicularly distance between the center of the spherical cavity and the central axis of the lead-through 110, i.e. the lead-through is not centered around the center of the spherical cavity of the joint socket.

Preferably, the central axis of the lead-through 110 does not cut any part of the spherically shaped cavity. The perpendicularly distance between the center of the spherical cavity and the central axis of the lead-through 110 is thus larger than the radius of the spherically shaped cavity. Accordingly, the ball socket of the dental implant will only occupy the lead-through 110 partly, when the superstructure is mounted on the dental implant.

The sleeve 111 may be fastened/secured to main portion 31 via a thread mating or by friction. When the sleeve 111 is fastened to the main portion by friction, the sleeve may for example be provided with a rubber or plastic on the surface intended to engage the lead-through 110. The sleeve 111 may have a tubular configuration, wherein the outer surface is intended to engage the lead-through 110, and the inner surface is intended to engage a screw member. Thus the inside surface of the sleeve 111 is threaded with a thread 112, to cooperate with a screw member.

Although FIG. 11, depicts an embodiment wherein the fastening socket is a joint socket, the use of a sleeve 111 to cooperate with a screw member, is not limited to embodiments wherein the fastening socket is a joint socket.

As the sleeve 111, and thus the thread 112, is separate from the main portion 31, treatment of the main portion 31, such as burning off the facing material on the main portion 31, prior to insertion of the sleeve 111 and the subsequent joining of the dental superstructure 300 and the dental implant 10, will not adversely affect the screw thread 112, which otherwise may be the case.

In one embodiment, the lead-through 110 and/or the sleeve 111 are conical. The conicity of the lead-through 110 is naturally such that the diameter increases towards the mouth of the lead-through. Thus the sleeve 111, once received in the lead-through 110, is fastened. Friction, alternatively according to above, will prevent the sleeve 111 from rotating.

In one embodiment, the lead-through 110 has protrusion (s), adapted to fasten the sleeve 111. Further, also the sleeve 111 may have protrusion(s).

In one embodiment the lead-through 110 and/or the sleeve 111 may have groove(s). In one embodiment, the lead-through 110 has protrusion(s), while the sleeve 111 may have groove(s). In such an embodiment the protrusion(s) may be adapted to engage the groove(s).

In one embodiment neither the lead-through 110 nor the outer surface of the sleeve 111, are cylindrical with respect to the central axis. By deviating from a cylindrical shape, the sleeve 111 will be prevented from rotating, once received in the lead-through 110.

According to one embodiment, the fastening portion 101 of a dental implant 10 or dental implant adapter 20 is accessed by an impression cap for making an impression of the positioning of the implant. The impression cap is fitted on the fastening portion 101 of the dental implant 10 or dental implant adapter 20, and the patient then bites a flexible material to make the impression caps stick to the flexible material. After the flexible material, with impression caps, have been removed, it is possible to see the angles at which the fastening portion of the dental implant are to be mounted.

Figure 7A:
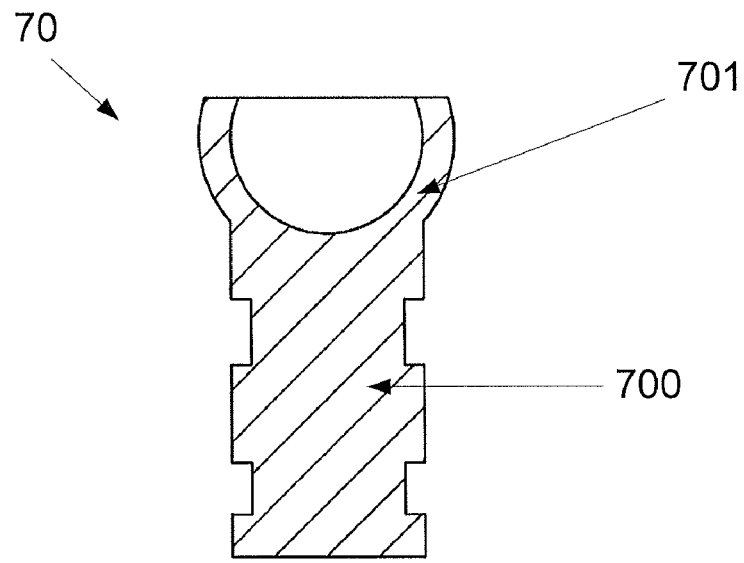
FIG. 7 is an illustration of an impression cap according to one embodiment of the invention.
Figure 7B:
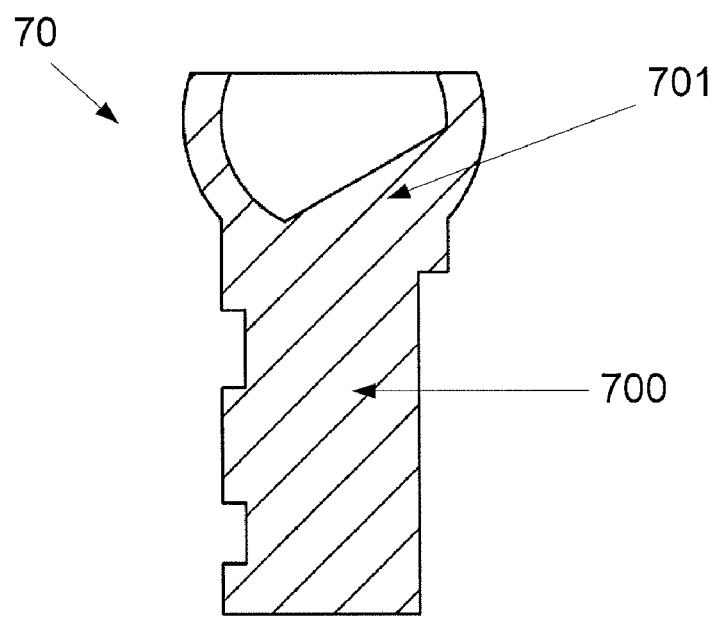

In an embodiment according to FIG. 7, an impression cap 70 for connection to a ball socket is disclosed. FIG. 7A is showing an impression cap with fully spherical geometry and FIG. 7B is showing an impression cap with a truncated spherical geometry. The impression cap comprises along its longitudinal axis, an impression portion 700 for making an impression in a soft material, and a fastening portion 701.

According to one embodiment, the fastening portion 701 is a joint socket.

In a further embodiment, the fastening portion 701 is a ball socket.

Figure 8:
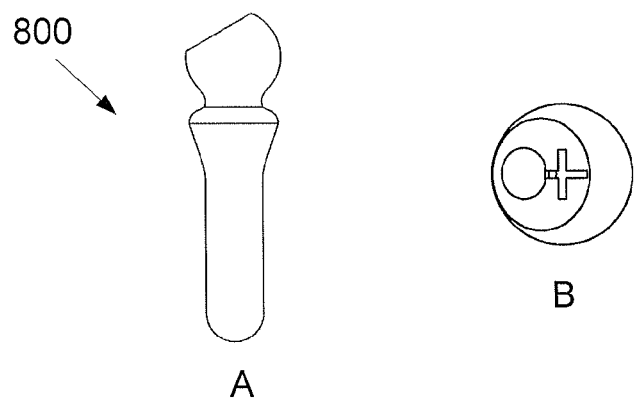
FIG. 8 is an illustration of a dental implant with a ball socket with truncated sphere.

In an embodiment according to FIG. 8, a dental implant with a ball socket with truncated sphere 800 is disclosed. FIG. 8A is showing the implant from the side and FIG. 8B is showing the implant from the top. The truncation of the sphere may be made with any angle with respect to the vertical axis of the implant. FIG. 8B also shows a driving portion with a cross.

Figure 9:
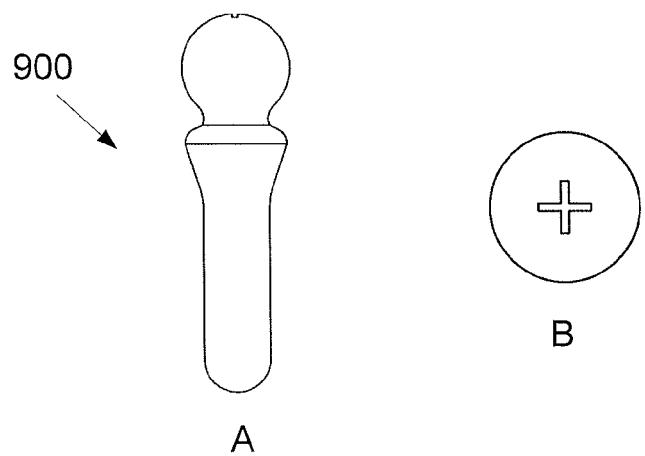
FIG. 9 is an illustration of a dental implant with a ball socket with full sphere.

In an embodiment according to FIG. 9, a dental implant with a ball socket with full sphere 900 is disclosed. FIG. 9A is showing the implant from the side and FIG. 9B is showing the implant from the top. FIG. 8B also shows a driving portion with a cross.

Figure 10:
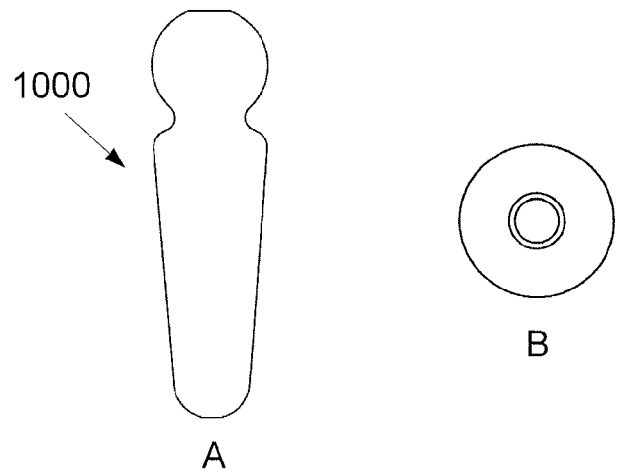
FIG. 10 is an illustration of a dental implant with a ball socket with horizontally truncated sphere.

In an embodiment according to FIG. 10, a dental implant with a ball socket with horizontally truncated sphere 1000 is disclosed. FIG. 10A is showing the implant from the side and FIG. 10B is showing the implant from the top. As will be appreciated by a person skilled in the art, the truncation may be made more or less extensive, as long as the implant is suitable for retaining the dental implant. FIG. 10B also shows a driving portion with a hole. According to a preferred embodiment, the whole is threaded on the inside. The threading may be adapted to suit the driving tool.

Although the present invention has been described above with reference to (a) specific embodiment(s), it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

The invention claimed is:

1. A superstructure for a dental implant, comprising:
   a fastening portion including a joint socket in the form of a spherically shaped cavity with a fastening surface; and
   a main portion;
   wherein the superstructure is configured to be joined to an osseointegrated dental implant via the fastening portion;
   wherein the main portion includes a hole for receiving a sleeve or a screw;
   wherein part of the hole forms an opening in the fastening surface, such that a perpendicular distance exists between the center of the spherically shaped cavity and the central axis of the hole.

2. The superstructure according to claim 1, wherein the central axis of the hole does not cut any part of the spherically shaped cavity.

3. The superstructure according to claim 1, wherein the superstructure comprises:
   a fastening part, suitable for fixating a ball socket of a dental implant, thus creating a ball joint; and
   control means operably connected to the fastening part, the control means for activating the fastening part.

4. The superstructure according to claim 3, wherein the control means comprises a screw member.

5. The superstructure according to claim 4, wherein the thread of the screw member is left hand threaded.

6. The superstructure according to claim 1, wherein the hole of the main portion is adapted to receive and fasten a separate sleeve.

7. The superstructure according to claim 6, wherein the superstructure comprises a sleeve in the hole, the inside of the sleeve being threaded.

8. The superstructure according to claim 7, wherein the sleeve is conical.

9. The superstructure according to claim 1, wherein the hole of the main portion is a screw hole.

10. The superstructure according to claim 1, wherein the hole of the main portion includes at least one protrusion.

11. The superstructure according to claim 1, wherein a ball joint is fastened to the osseointegrated dental implant by one of the methods chosen from the group consisting of clamp, friction grip, screw anchoring, and a combination of screw anchoring and friction grip.

12. A dental implant system, comprising a dental implant and a superstructure joined with a ball joint, wherein the superstructure is according to claim 1.

13. A dental implant system, comprising a dental implant adapter and a superstructure joined with a ball joint, wherein the superstructure is according to claim 1.

* * * * *